(12) United States Patent
Reeves et al.

(10) Patent No.: US 8,551,746 B2
(45) Date of Patent: *Oct. 8, 2013

(54) METHOD FOR CONTROLLING UNDESIRABLE BYPRODUCTS FORMATION CAUSED BY CONTAMINATING ORGANISMS IN THE PRODUCTION OF ETHANOL FROM SYNGAS

(75) Inventors: Andrew Reeves, Chicago, IL (US); Rathin Datta, Chicago, IL (US)

(73) Assignee: Coskata, Inc., Warrenville, IL (US)

( * ) Notice: Subject to any disclaimer, the term of this patent is extended or adjusted under 35 U.S.C. 154(b) by 53 days.

This patent is subject to a terminal disclaimer.

(21) Appl. No.: 13/239,305

(22) Filed: Sep. 21, 2011

(65) Prior Publication Data

US 2013/0071896 A1  Mar. 21, 2013

(51) Int. Cl.
*C12P 7/52* (2006.01)
*C12P 7/06* (2006.01)

(52) U.S. Cl.
USPC ............ 435/140; 435/161; 435/157; 435/141

(58) Field of Classification Search
USPC .................. 435/162, 7.1, 140, 141, 157, 161
See application file for complete search history.

(56) References Cited

U.S. PATENT DOCUMENTS

| | | |
|---|---|---|
| 7,285,402 B2 | 10/2007 | Gaddy et al. |
| 2009/0215163 A1 | 8/2009 | Tsai et al. |
| 2011/0059499 A1 | 3/2011 | Simpson et al. |
| 2011/0229947 A1 | 9/2011 | Zahn et al. |

*Primary Examiner* — Chih-Min Kam

(57) ABSTRACT

A method of operating a fermentation zone for the production of ethanol from syngas uses a crotonate derivative to prevent or reverse the effects of butyrigen contamination. The crotonate compound works in continuous fermentation processes to reduce or eliminate contamination from butyrate and butanol in the syngas derived ethanol product.

21 Claims, 6 Drawing Sheets

METHOD FOR CONTROLLING UNDESIRABLE BYPRODUCTS FORMATION CAUSED BY CONTAMINATING ORGANISMS IN THE PRODUCTION OF ETHANOL FROM SYNGAS

FIELD OF THE INVENTION

This invention pertains to processes for the low energy, anaerobic bioconversion of hydrogen and carbon monoxide in a gaseous substrate stream to oxygenated $C_2$ compounds such as ethanol by contact with microorganisms in a fermentation system with high conversion efficiency of both hydrogen and carbon monoxide. The method of this invention reduces production of undesirable byproducts such as butyric acid, butanol and other longer chain organic acids or alcohols that result from bacterial contaminants in the fermentation system.

BACKGROUND

Bioethanol production for use as a liquid motor fuel is increasing worldwide. Such biofuels include, for example, ethanol that can be blended with gasoline with a wide range of compositions. One of the major drivers for bioethanol is its derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues are looked to as feedstocks for biofuel production. Unlike utilization of fossil fuels, deriving bioethanol from such plant or even municipal waste sources provides an environmentally sustainable resource for the production of liquid fuels.

A highly efficient route to the production of bioethanol is the gasification of biomass or other organic matter into a substrate gas comprising CO and/or hydrogen followed by the conversion of the gas to ethanol using homoacetogenic microorganisms. Methods for such conversion are known from U.S. Pat. No. 7,285,402 B2, US 20110059499 A1, US 20090215163 A1, and others.

Typically the substrate gas for carbon monoxide or hydrogen conversions is derived from a synthesis gas (singes) from the gasification of carbonaceous materials, reforming of natural gas and/or biogas from anaerobic fermentors or from off streams of various industrial methods. The gas substrate contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

Production of ethanol from the substrate gas by these methods requires significant amounts of hydrogen and carbon monoxide. For instance, the theoretical equations for the conversion of carbon monoxide and hydrogen to ethanol are:

$6CO + 3H_2O \cdot C_2H_5OH + 4CO_2$

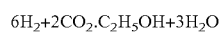

$6H_2 + 2CO_2 \cdot C_2H_5OH + 3H_2O$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Syngas fermentation processes suffer from the poor solubility of the gas substrate, i.e., carbon monoxide and hydrogen, in the liquid phase of the fermentation menstruum. Munasinghe, et al., in *Biomass-derived Syngas Fermentation in Biofuels: Opportunities and Challenges, Biosource Technology*, 101 (2010) 5013-5022, summarize volumetric mass transfer coefficients to fermentation media reported in the literature for syngas and carbon monoxide in various reactor configurations and hydrodynamic conditions. As a result biofermentation processes for the production of ethanol will require large volumes of fermentation liquid. For example commercial scale plants, those with capacities of 55 million gallons or more, will require fermentation zones that utilize vessels holding a million gallons or more of the fermentation liquid.

To maintain the efficiency of producing ethanol by such fermentation zones there is a need to maximize the production of $C_2$ oxygenated products while minimizing the production of higher carbon chain products such as $C_4$, $C_6$, $C_8$ and higher organic acids or alcohols. The known methods seek to accomplish this efficiency by utilizing homoacetogenic bacteria that have a very high degree of selectivity for the production of $C_2$ products. By their nature the homoacetogenic organisms that convert the gas substrate to ethanol do not have the pathways to make these longer carbon chain products.

The ability of homoacetogenic organisms to survive with minimal media on the CO and $H_2$ substrate under anaerobic condition provides a protection against many biological contaminants that require much different environments. However, the size and scale of the fermentation zones and overall facilities necessary for the production of ethanol on a commercial basis precludes axenic operation of the facilities. As a result microbial contamination will inevitably occur at some point and can degrade the production by producing such higher chain byproducts that can result in 20 percent or more of byproducts and thus severely reducing the yield of ethanol, or other desirable products.

While there are many potential contaminants, one class of potentially common contamination will produce butyric acid, butanol and other longer chain organic acids or alcohols. Microorganisms that produce such compounds as part of their primary metabolism are referred to as butyrigens. There are many classes of butyrigens. A major class utilizes carbohydrates and other carbon compounds such as amino acids, lipids, etc. Another class of butyrigens uses syngas and yet another class of butyrigens can utilize ethanol and acetate with transferase enzyme pathways. Since, for the reasons previously mentioned, it is not possible to operate such large fermentation axenically, all of these butyrigen contamination sources will exist.

Once the butyrigen contamination takes hold in a large scale fermentation vessel it can destroy the commercial viability of the process by shifting feed conversion from desired products and making product recovery impractical. Designing product recovery facilities for wide variations in composition and concentration of liquid compounds will add prohibitive cost. The large volume of the fermentation liquid and the time to incubate the microorganisms to production concentrations make flushing and restarting of the facility impractical as well.

Therefore methods are sought to eliminate or inhibit the growth of butyrigens in a large scale fermentation zone without disrupting the ongoing production of ethanol or other products such as acetic acid, propanol, or propionic acid from such a fermentation zone.

SUMMARY

By this invention a class of crotonate compounds have been found to inhibit the growth of a butyrigen population while not disrupting the productivity of light oxygenate products such as ethanol, acetic acid, propanol, and propionic acid by homoacetogenic or heteroacetogenic microorganisms. Achieving this discovery required the identification that these compounds act as bacteriostatic or bacteriocidal agents to the butyrigens while not inhibiting the growth of the homoacetogens. Whether the compound acts as a bactericide or bacteriostatic agent, its ability to act in vivo is equally important for its effectiveness in preserving production of desired products in a large scale fermentation zone. The discovered class of compounds was found to be effective in vivo and therefore will act to inhibit or retard butyrigen contamination within the fermentation vessel and may be introduced as an additive in the process as needed. Crotonate derivatives that act in bacteriocidal or bacteriostatic manner of this invention are referred to herein as butyl retardants.

Effective crotonate compounds include di-halogen substituted crotonate compounds. The di-halogen substituted crotonate compounds include acid and esters. Specific compounds include Ethyl 4,4,4, Triflouromethyl 3(trifluromethyl)crotonate, 4,4,4,trifluoro 3-(triflouromethyl)crotonic acid, Ethyl 4,4,4,trifluoromethyl 3-(trichloromethyl)crotonate, 4,4,4,trifluoromethyl 3-(trichloromethyl)crotonic acid, Ethyl 4,4,4 trichloromethyl 3-(trifluoromethyl)crotonate, 4,4,4 trichloromethyl 3-(trifluoromethyl)crotonic acid Ethyl 4,4,4 trichloromethyl 3-(trichloromethyl)crotonate, 4,4,4 trichloromethyl 3-(trichloromethyl)crotonic acid, 4,4,4, tribromomethyl 3-(trifluoromethyl)crotonic acid, Ethyl 4,4,4 tribromomethyl 3-(trifluoromethyl)crotonate, 4,4,4 trifluoromethyl 3-(tribromomethyl)crotonic acid, 4,4,4 trichloromethyl 3-(tribromomethyl)crotonic acid, 4,4,4, triiodomethyl 3-(trifluoromethyl)crotonic acid, Ethyl 4,4,4 triiodomethyl 3-(trichloromethyl)crotonate, 4,4,4 trifluoromethyl 3-(triiodomethyl)crotonic acid, 4,4,4 trichloromethyl 3-(triiodomethyl)crotonic acid.

The effect of the crotonate compounds varied with their concentration. In accordance with this invention the crotonate compounds will be effective in fermentation process with a concentration of the pure compound of as little as 50 ppm to inhibit the growth of the butryigens. Effective concentrations may be reduced significantly with the use of delivery systems and agents that improve the uptake of the compounds by the microorganisms. In most cases concentrations in excess of 1000 ppm are avoided so as to not hinder the growth of the microorganisms that are producing the light oxygenates such as ethanol.

A broad aspect of this invention is a method of restricting the production of butyrate and butanol in an anaerobic fermentation of a gas substrate that comprises at least one of CO and/or a mixture of $CO_2$ with hydrogen. The method passes the gas stream to an anaerobic fermentation zone containing at least one species of anaerobic microorganism capable of producing an oxygenated liquid product other than or in addition to butyrate and butanol. At least a portion of the gas stream is converted to the liquid product by contact of the microorganism in the fermentation zone with the gas stream.

A di-halogen substituted crotonate ester and/or acid is added to the fermentation liquid as a butyl retardant in an amount effective to restrict production of butyrate and butanol. The method withdraws a fermentation liquid containing the liquid product from the fermentation zone and recovers the liquid product from the fermentation liquid. The fermentation zone will usually contain multiple species of microorganisms, typically a homoacetogenic microorganism for the production of a liquid product and a butyrigenic microorganism that produces butyrate and/or butanol. The fermentation zone may also contain heteroacetogenic microorganisms that produce a butyrate or butanol as well as a liquid product such as acetic acid and/or ethanol.

Another broad aspect of this invention is a method of producing ethanol by the fermentation of a gas stream that contains CO and/or a mixture of $CO_2$ with hydrogen using a homoacetogenic microorganism to convert the gas stream wherein the production of butyrate is inhibited. The method passes the gas stream to a fermentation zone containing a homoacetogenic microorganism and a fermentation liquid. Contact of the homoacetogenic microorganism with the gas stream produces ethanol in the fermentation zone. A di-halogen substituted crotonate acid or ester is introduced into the fermentation liquid in a sufficient amount to inhibit the growth of butyrigens and the production of butyrate and butanol. The butyl retardant concentration may range between 10 and 1000 ppm on an intermittent or continual basis. The method withdraws ethanol containing fermentation liquid from the fermentation zone and an ethanol product is recovered from the fermentation liquid.

In another form this invention is a method for producing ethanol by the fermentation of a gas stream that contains CO and/or a mixture of $CO_2$ with hydrogen using a homoacetogenic microorganism to convert the gas stream to ethanol. The method passes the gas stream to a fermentation zone containing the homoacetogenic microorganism and a fermentation liquid that converts the gas stream to ethanol by contact with the homoacetogenic microorganism. A butyl retardant comprising a di-fluoro substituted crotonate compound is added to the fermentation zone to disrupt the growth of butyrate producing microorganisms. The butyl retardant is added in an amount that produces a concentration of the di-fluoro substituted crotonate compound in a range of between 50 and 1000 ppm. The method withdraws the ethanol containing fermentation liquid from the fermentation zone and an ethanol product is recovered from the fermentation liquid. In a preferred form of the invention the butyl retardant comprises Ethyl 4,4,4, Triflouromethyl 3(trifluromethyl)crotonate and it is added to the fermentation zone at a concentration of 50 to 500 ppm.

FIGURES

DETAILED DESCRIPTION

Definitions

Figure 1:
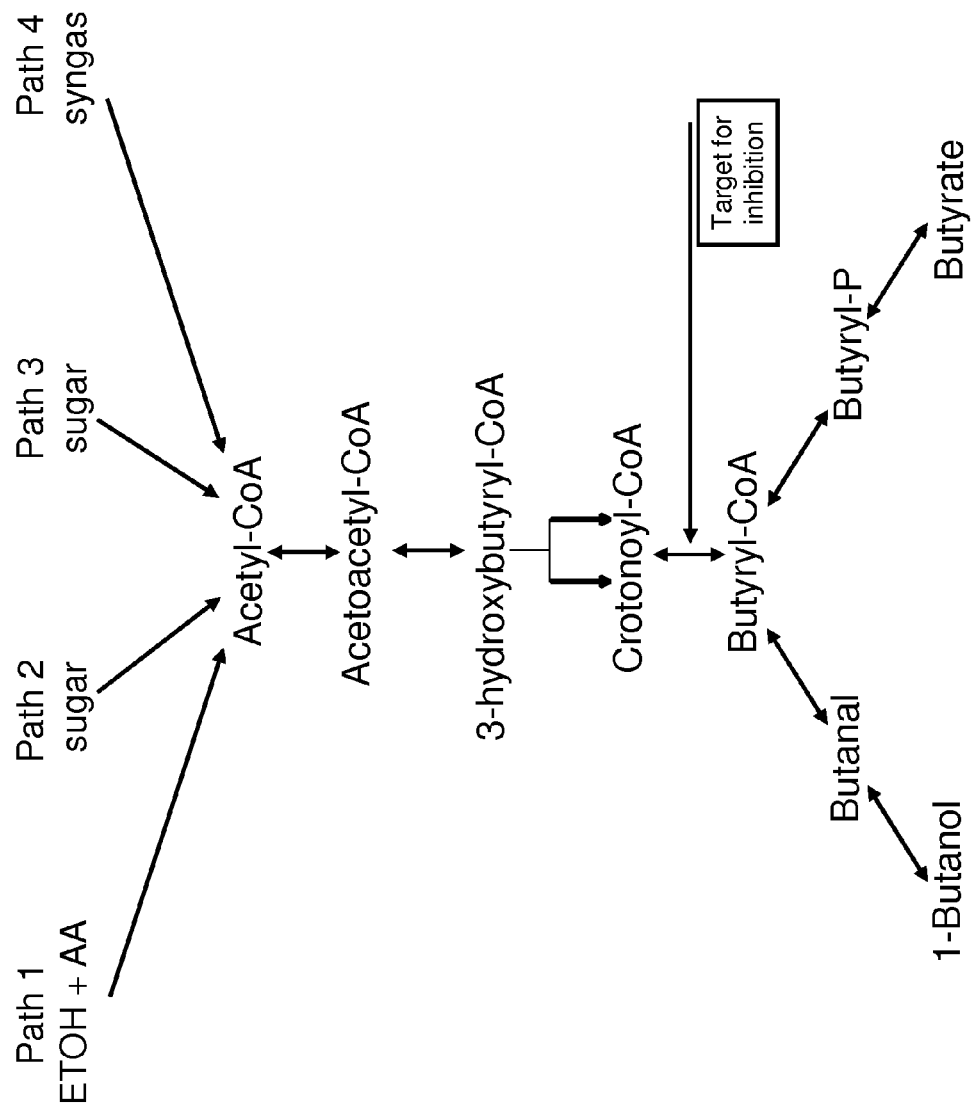
FIG. 1 is diagram illustrating some key enzymes products and intermediate products in butyrigen metabolism for producing butanol and butyrate.
Figure 2:
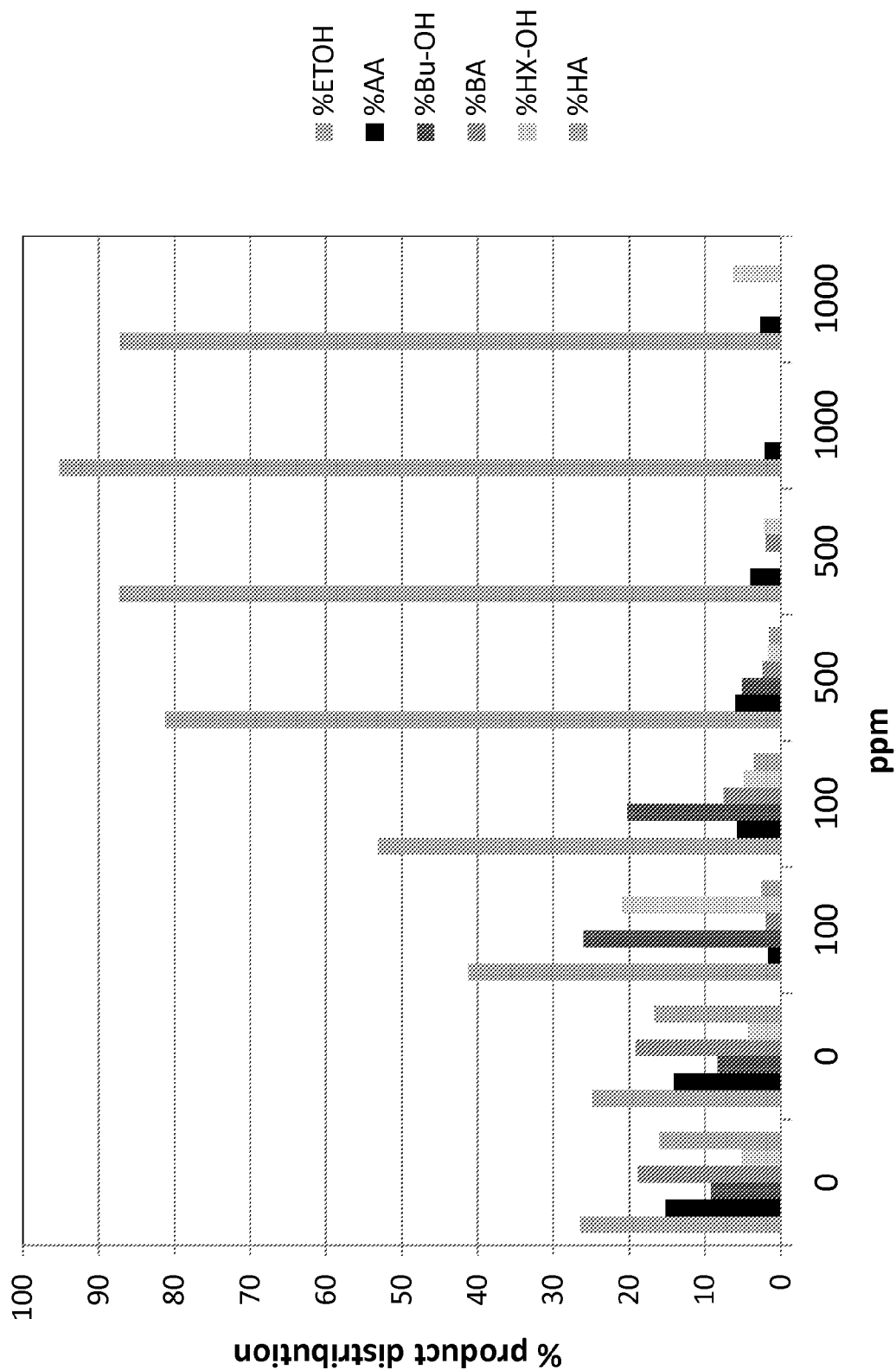
FIG. 2 is a bar graph showing the product distribution from fermentations with heteroacetogenic bacteria in the presence of varying concentrations of a crotonate derivative.

Butyrigens refer to microorganisms that under anaerobic conditions produce compounds having four carbon atoms such as butyrates and butanol and the term can also include longer chain ($C_6$-$C_8$) organic acids and alcohols.

Butyl retardant refers to a compound that is used to inhibit or kill the butyrigens. The term contemplates the activity of the compound as a bactericide or bacteriostatic agent.

Butyl impurity refers to any molecule that has a total of four or more carbon atoms in its structure with the carbon atoms arranged as a chain.

Light oxygenates refers to any molecule that has two or three carbon atoms and at least one carbon-oxygen bond.

General Description

This invention applies to anaerobic fermentations to produce light oxygenates such as ethanol, acetic acid, propanol, and propionic acid using a gas substrate comprising carbon monoxide and hydrogen, and the gas will typically contain carbon dioxide and nitrogen. Syngas is one source of such a gas substrate. Syngas can be made from many carbonaceous feedstocks. These include sources of hydrocarbons such as natural gas, biogas, gas generated by reforming hydrocarbon-containing materials, peat, petroleum coke, and coal. Other sources for production of syngas include waste material such as debris from construction and demolition, municipal solid waste, and landfill gas. Syngas is typically produced by a gasifier. Any of the aforementioned biomass sources are suitable for producing syngas. The syngas produced thereby will typically contain from 10 to 60 mole % CO, from 10 to 25 mole % $CO_2$ and from 10 to 60 mole % $H_2$. The syngas may also contain $N_2$ and $CH_4$ as well as trace components such as $H_2S$ and COS, $NH_3$ and HCN. Other sources of the gas substrate include gases generated by petroleum and petrochemical processing. These gases may have substantially different compositions than typical syngas, and may be essentially pure hydrogen or essentially pure carbon monoxide. Also, the substrate gas may be treated to remove or alter the composition including, but not limited to, removing components by sorption, membrane separation, and selective reaction. Components may be added to the gas substrate such as nitrogen or adjuvant gases such as ammonia and hydrogen sulfide. The term syngas will be used herein and will be intended to include these other gas substrates.

This invention will use homoacetogenic microorganisms and fermentation conditions particularly selected for the production of light oxygenates and preferably selected for the production of ethanol. Bioconversions of CO and $H_2/CO_2$ to acetic acid and ethanol and other products are well known. Suitable microorganisms live and grow under anaerobic conditions, meaning that gaseous and dissolved oxygen is essentially absent from the fermentation zone. A concise description of biochemical pathways and energetics for acetogenic bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any microorganisms that have the ability to produce ethanol by converting the syngas components: CO, $H_2$, $CO_2$ individually or in combination with each other or with other components that are typically present in syngas may be utilized. Suitable microorganisms and/or growth conditions may include those disclosed in U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622 which is incorporated herein by reference in its entirety. *Clostridium ragsdalei* may be used, for example, to ferment syngas to ethanol.

Suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edmond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Ser. No 12/272,320 on Mar. 19, 2010. All of these references are incorporated by reference herein in their entirety.

The invention can provide benefit for any type of fermentation zone. Suitable fermentation zones are typically referred to as a bioreactor. The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fiber Membrane Bioreactor (HFMBR), Static Mixer, or other vessel or other device suitable for gas-liquid contact.

Typical bioreactors have the arrangement of a suspended cell type bioreactor or membrane supported bioreactor. In a suspended cell type bioreactor the fermentation liquid contains the microorganisms in suspension as the gas substrate passes through the fermentation liquid to effect contacting between the gas and the microorganisms by absorption of the gas into the liquid and uptake of the dissolved gas by the microorganism. Suspended cell bioreactors typically take the form of a continuous stirred tank where impellers provide mechanically mix the gas substrate and the fermentation liquid or a bubble column bioreactor where the injection of the substrate into the gas promotes mixing of the gas and liquid.

A membrane supported bioreactor utilizes a solid surface upon which to grow the microorganisms as a biofilm or a concentration of cells that the substrate gas contacts. One membrane bioreactor, as shown in US 20080305539 A1, grows the biofilm on one side of the membrane and in direct contact with the fermentation liquid while the substrate gas permeates into contact with the biofilm from the opposite side of the membrane. US 20090215163 A1 discloses the opposite arrangement for a membrane supported bioreactor where one side of the membrane retains the microorganisms in direct contact with the gas substrate while the fermentation liquid permeates from the opposite of the membrane and into contact with the microorganisms. Either type of membrane supported bioreactor is suitable for use with this invention.

When using the invention with a suspended cell bioreactor the fermentation liquid will include a suspension of microorganisms and various media supplements. The various adjuvants to the fermentation liquid may comprise buffering agents, trace metals, vitamins, salts etc. Adjustments in the fermentation liquid may induce different conditions at different times such as growth and non-growth conditions which will affect the productivity of the microorganisms. Previously referenced U.S. Pat. No. 7,704,723, the contents of which are hereby incorporated by reference, discloses the conditions and contents of suitable fermentation menstruum for bioconversion of CO and $H_2/CO_2$ using anaerobic microorganisms. Other methods, operating conditions and media for operating bioreactors to produce ethanol are described in the literature that includes those described in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

The fermentation is carried out under appropriate conditions that include pressure, temperature, gas flow rate, liquid flow rate, media pH, media redox potential, agitation rate (if using a continuous stirred tank reactor), inoculum level, and maximum gas substrate concentrations to ensure that CO in the liquid phase does not become limiting, and maximum product concentrations to avoid product inhibition. Suitable conditions are described in WO02/08438, WO07/117,157 and WO08/115,080. Typically, the fermentation liquid and the microorganisms in the fermentation zone include a suitable temperature in the range of between 25° C. and 60° C., and more frequently in the range of about 30° C. to 40° C. Other conditions of fermentation include the density of microorganisms, fermentation liquid composition, and liquid depth, which are all preferably sufficient to achieve the sought conversion of hydrogen and carbon monoxide.

Fresh liquid media containing nutrients will typically enter the bioreactor on a continual basis. The addition of the fresh media and the withdrawal of fermentation liquid provide a continual withdrawal of cell mass from the bioreactor. As the fermentation continues to generate cell mass, the removal and addition rate of media and fermentation liquid will establish a mean cell retention time in the bioreactor. Mean cell retention times for most fermentation zone are typically in a range of from 2 to 7 days.

The butyl retardant as described in this invention is a class of compounds that has the effect of inhibiting or stopping the production of acids or alcohols with four or longer chain carbon atoms by microorganisms in a fermentation zone while not substantially interfering with the conversion of syngas to lower carbon number oxygenates such C2 and C3 acids and alcohols. Useful butyl retardants are any compounds that can interfere with the butyl impurity production of one or more butyrigens. Known butyrigens include the strict butyrigens that produce essentially only butyl impurities and heteroacetogens that can produce ethanol and acetate along with butyl impurities.

Butryrigens are characterized by having a critical step of in their metabolic pathway for the conversion of crotonyl CoA to butyryl CoA. FIG. 1 shows generalized pathways for butyrigen metabolism and that the pathways for production of butanol and butyrate differ only in the starting substrates. The starting substrates to the production of butanol and butyrate include ethanol and acetic acid through path 1, sugar through path 2 and 3, and syngas through path 4.

Butyrigens such as *C. acetobutylicum*, make a butyrate as a primary product or as a smear of short-chain fatty acid products as part of their primary metabolism in which several acids and their corresponding solvents are also produced (FIG. 1, Path 2). These organisms use sugars or proteins as substrates for metabolite production. Other butyrigens, such as various *Eubacterium* strains and *Roseburia* are strictly butyrogenic and produce large amounts of the acid by using a different enzyme to generate the final product, butyrate (FIG. 1, Path 3). These classes of butyrigens are predicted to be less problematic than those that use Path 1 and Path 4 since they may be metabolically disadvantaged under the growth conditions predicted to exist in large-scale syngas reactors.

Path 1 (FIG. 1) encompasses *C. kluyveri* and similar metabolic types of organisms that can use ethanol, acetate and hydrogen to make $C_4$ and higher chained acids. *C. kluyveri* can reside in a reactor and form a commensal relationship with other organisms, thus potentially making it metabolically advantaged and which can lead to persistent infections if the fermenter's environmental conditions are not altered. Thus, of the non-syngas using butyrigens, *C. kluyveri* and similar types pose a high risk for long-term, persistent contamination since they can readily make $C_4$ or higher acids from ethanol and acetate or two acetates. This reaction is also thermodynamically advantaged under certain conditions.

Finally, organisms that use Path 4 (FIG. 1) are those that can grow on both sugars and syngas and produce a variety of short chain and higher chain acids and alcohols. These are broadly classified as the heteroacetogens and members include *C. carboxidivorans* and *C. drakei*. These heteroacetogens can use either sugars as well as syngas substrates and can also make $C_4$ acids and solvents from C2 subunits. The heteroacetogens pose a slightly higher risk than other butyrigens, since they may be metabolically advantaged under the low redox, high dissolved syngas conditions that would exist in a large-scale fermentation zone.

As with the strict butyrigens, the heteroacetogens use a common pathway to generate $C_4$ compounds. The entry point into butyrigenesis, which is a highly conserved pathway except for a few endpoint reactions among all butyrigens, occurs when two acetyl-CoAs condense to form acetoacetyl-CoA by a reaction with thiolase. This is followed by a hydroxylation at one of the carbonyls to form S3-hydroxybutyryl-CoA (FIG. 1). Hydroxybutyryl-CoA is dehydrated by crotonase to form crotonyl-CoA. The previous reaction to form 3-HBCoA can be achieved by a variety of dehydrogenases and does not generate any energy for the cell, but it does regenerate some oxidized cofactor. Once the crotonyl-CoA is generated the cell becomes susceptible to inhibitors since most, if not all, of the energy derived from butyrogenesis comes from the conversion of crotonyl-CoA to butyryl-CoA. All of these pathways are stopped by disrupting the critical step of converting the crotonyl CoA to butyryl CoA.

It was found that a class of crotonate compounds would act as butyl retardants in the production of light oxygenates from syngas. It is believed that these compounds interrupt this critical step in the butyrigen metabolism. Specifically crotonate esters and acids having a disubstitution of halogenenated methyl groups were found to inhibit the growth of strict butyrigens and heteroacetogens. At the same time, this crotonate ester did not interfere with the production of light oxygenates such as ethanol by a homoacetogen. Importantly, the deleterious effect on the butyrigen occurred in vivo thereby making this retardant suitable for direct use in fermentations.

Although not wishing to be bound by any theory, the halogenated moieties of the molecule are believed to disrupt the enzyme activity at the essential Crotonyl CoA to Butyryl CoA step. This disruption is believed to be caused by the dihalogenated crotonate compounds ability to mimic the crotonate molecule and interfere with the catalytic activity of the enzyme. On this basis, the di-halogenated crotonate esters and acids will generally have the effect of interrupting this step.

These butyrigen retardants operate at a relatively low concentration level. At concentrations as low as 50 ppm in a continuous fermentation the crotonate derivatives had beneficial effects on reducing butanol and butyric acid while not disrupting the production of acetic acid and ethanol. In fact it has been discovered that crotonate derivatives do not begin to impact homoacetogen growth until reaching concentrations of 1000 ppm in the fermentation liquid. Thus, the amount of the crotonate derivative added to the fermentation zone can be adjusted to maintain it in a range that will effectively retard the growth of the butyrigens without inhibiting the growth of desired homoacetogens. As a result use of the butyl retardant can be tuned to curtail the production of butyl impurities while not harming the production of ethanol, acetic acid and other light oxygenate products.

The butyl retardant may be added to a fermentation zone in a variety of ways. It may be injected in a desired dosage directly into the fermentation zone. The butyl retardant may also be mixed with the fresh media input or a recycle stream from the fermentation zone to promote better mixing of the butyl retardant in the fermentation zone.

These butyl retardants and readily miscible in simple hydrocarbons and other non-aqueous solvents. For example common aromatic hydrocarbons such as xylenes, toluene etc. or aliphatic hydrocarbons such as hexane dissolve these butyl retardants. Hence these can be dissolved in such hydrocarbon and other non-aqueous solvents and made into microemulsions by well-known techniques by addition of suitable surfactants and cosolvents. These microemulsion particles are typically 0.1 micron in diameter and can be readily dispersed into the fermentation medium. There these emulsion particles will contact with the butyrigens and deliver the butyl retardants to the organisms. The major advantage of such microemulsion delivery system is that they are effective in much lower dosages because they can protect the active compounds such as the butyl retardants and also deliver them to the cell surface which is the primary target. Methods for making such microemulsions and their usage in general biocide formulations have been described in U.S. Pat. No. 6,096,225 by Yang et al. In a suspended cell or planktonic type fermentation the butyl retardant will be effective when introduced as a single dose at a concentration of from 10 to 1000 ppm with concentration levels of 50 to 500 ppm being preferred for most applications. The effective concentrations will be influenced by the delivery system with microemulsion systems having effective concentration below 50 ppm and down to 10 ppm or lower. Preferably these dosages are calculated based on the mean cell retention time of the bioreactor such that the dosage will have a duration of at least 2 days.

It is possible to add the butyl retardants in varied amounts in response to monitoring of butyl impurity production and the $C_2$ product output and making adjustments in addition and concentration depending upon the production of the butyl impurities. In this respect the desired amount of butyl retardant can be added to maintain a desired concentration in a fermentation zone or in response to monitoring the presence of butyrigen contamination. Thus, the butyl retardant may be used continually or intermittently to prevent or reverse the effect of butyrigen growth. If desired, the butyl retardant may be added at the start of the of a fermentation process. In this manner the butyl retardant acts as a prophylactic measure to prevent butytrigen contamination from taking hold in the fermenter. The addition may be continued throughout the fermentation process by continuous or intermittent injection of the butyl retardant into the fermentation zone. In such cases a relatively low butyl retardant dosage can be effective. In particular, intermittent dosages at a concentration level of 50 ppm or preferably 50 to 100 ppm on a frequency of 5 to 10 days may be used. In the absence of recovery and recirculation of liquid containing the butyl retardant, the butyl retardant will wash out of the bioreactor at a rate determined by the mean cell retention time.

Regardless of the delivery system any method may be used to determine the presence of butyrigens and the effectiveness of the butyl retardant. Monitoring of the product output for the presence of butyl impurities from the fermentation zone can provide an indication of butyrigen contamination. Preferably the fermentation liquid will undergo periodic sampling for detection of butyl impurities.

Most often the butyl retardant is added in response to the detection of the butyrigens. In this case the butyl retardant is added in sufficient amount to produce a single dose in a concentration of 100 to 1000 ppm in the fermentation zone, with a dose in the range of 500 to 1000 ppm being preferred. A desired concentration of crotonate compound may be maintained until the presence of the butyrigens has been reduced to a desired level as typically indicated by the production of butyl impurities from the fermentation zone. Once sufficient butyrigens have been reduced to a level that produces an acceptable fermentation zone product, the crotonate compound can be allowed to wash out of the fermentation zone.

The butyl retardant can be introduced to achieve a desired reduction in the amount of butyl impurities. Ideally, the butyl impurities in the in the fermentation liquid are reduced to zero, however, the fermentation liquid will typically contain some amount of butyl contamination. In most cases the butyl retardant will be used as necessary to keep the butyrate and butanol concentration in the ethanol containing fermentation liquid below 0.1% and preferably below 0.01%.

EXAMPLES

Examples 1-5

A variety of crotonate derivatives were tested for their bactericide or bacteriostatic activity. The tested compounds are identified in Table 1.

TABLE 1

| | |
|---|---|
| A. Ethyl 4,4,4, trifluoromethyl 3-(trifluoromethyl) crotonate | 236.12 |
| B. Ethyl-3-methylamino-4,4,4-trifluorocrotonate | 182.14 |
| C. Tert-butyl crotonate | 142.20 |
| D. 4,4,4-Trifluoro-3-(trifluoromethyl) crotonic acid | 208.06 |
| E. Ethyl 4,4,4-trifluorocrotonate | 168.12 |
| F. Ethyl-2-methyl-4,4,4-trifluorocrotonate | 197.16 |
| G. 4,4,4-trifluorocrotonic acid | 140.06 |
| H. Ethyl 3-aminocrotonate | 129.16 |

Example 1

These compounds were first tested to determine their effect on a known homoacetogen. Each compound was tested in a series of batch experiments to determine the growth response of a homoacetogen to the presence of the compound at varying concentrations. The batch experiments were all conducted by anoxically filling a Balch tube with 5 ml of a fermentation medium having the composition given in Tables 2 and 3. To expedite results, these batch experiments used fructose as the growth nutrient source for bacteria. Thus, the media included a 5 g/L of fructose.

TABLE 2

Fermentation Medium Compositions

| Components | Amount per liter |
|---|---|
| Mineral solution, See Table 3(a) | 25 ml |
| Trace metal solution, See Table 3(b) | 10 ml |
| Vitamins solution, See Table 3(c) | 10 ml |
| Yeast Extract | 0.5 g |
| Adjust pH with NaOH | 6.1 |
| Reducing agent, See Table 3(d) | 2.5 ml |

TABLE 3(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| $Na_2S \cdot 9H_2O$ | 40 |

Each tube was inoculated with 0.5 ml of the same strain of *C. autoethanogenum* bacteria seed culture inoculum. The tubes were maintained at a temperature of 37° C. Twenty one hours after the inoculation of the tube with the bacteria, the different crotonate derivatives from Table 1 were added to different tubes in the amounts indicated in Table 4 This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 190 hours. Growth at the intervals was measured by reading the optical density (OD) of the fermentation liquid. Optical density was measured using a Spectronic Spec 20 (Thermo Spectronic at a wavelength of 600 nm. The OD of the Balch tube culture was measured directly in the tube using absorbance mode on the Spec 20 machine. The machine was set to zero absorbance by first measuring and adjusting the setting to zero absorbance using media only as a blank. This process was repeated at each indicated time point throughout the experiment. The ability of a tube fermentation at a particular concentration of crotonate derivative to reach a predetermined optical density was recorded in Table 4. Table 4 indicates the presence of bacterial growth to an OD of approximately 2 or above with a "+", and to an optical density in a range of 0.5 to 1.5 as a "+/−", and indicates the failure of bacterial growth to reach an optical density of approximately 0.5 as a "−".

TABLE 4

| | ppm | | | | | | | | | |
|---|---|---|---|---|---|---|---|---|---|---|
| | 0 | 1 | 5 | 10 | 50 | 100 | 500 | 1000 | 5000 | 10000 |
| A | + | + | + | + | + | + | + | + | − | − |
| B | + | + | + | + | + | + | + | + | +/− | − |
| C | + | | + | | + | + | + | + | + | − |
| D | + | | + | | + | + | + | +/− | − | − |
| E | + | | + | | + | + | + | + | − | − |
| F | + | | + | | + | + | + | + | +/− | − |
| G | + | | + | | + | + | + | +/− | − | − |
| H | + | | + | | + | + | + | + | + | + |

As the Table 4 indicates, the homoacetogenic bacteria tolerated the presence of the tested crotonyl compounds up to concentrations of about 5000 ppm.

Example 2

Compounds A and D were again tested to determine their effect on another known homoacetogen. Each compound was tested in a series of batch experiments to determine the growth response of the homoacetogen to the presence of the compound at varying concentrations. These batch experiments were again all conducted by anoxically filling a Balch tube with 5 ml of a fermentation medium having the composition given in Tables 2 and 3. To expedite results, these batch experiments used fructose as the growth nutrient source for bacteria. Thus, the media included 5 g/L of fructose.

Each tube was inoculated with 0.5 ml of the same strain of *C. coskatii* bacteria seed culture inoculum. The tubes were maintained at a temperature of 37° C. Twenty one hours after the inoculation of the tube with the bacteria, the different crotonate derivatives from Table 1 were added to different tubes in the amounts indicated in Table 5 This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 50 hours. Growth at the intervals was determined by measurement of the OD in the manner described in Example 1. The ability of a tube fermentation at a particular concentration of crotonate derivative to reach a predetermined optical density was recorded in Table 5. Table 5 indicates the presence of bacterial growth to an OD of approximately 1.6 or above with a "+". All the samples of C. Coskatii reached a relatively high OD after a time of only 50 hours.

TABLE 5

| ppm | 0 | 100 | 500 | 1000 |
|-----|---|-----|-----|------|
| A   | + | +   | +   | +    |
| D   | + | +   | +   | +    |

Example 3

Similar experiments were conducted to make a preliminary determination as to which of the crotonate derivatives would act as butyrigen retardants. For this purpose the selected compounds were tested again in a series of batch experiments to determine the growth response of butyrigens to the presence of the compound at varying concentrations. The batch experiments were all conducted by anoxically filling a 20 ml Balch tube with 5 ml of a fermentation medium having the composition given in Tables 2 and 3. The media included 0.5 v/v final concentration of a fructose substrate. For each of the crotonate concentrations tested, duplicate test tubes were prepared.

Each tube was inoculated with 0.5 ml seed culture inoculum of the strict butyrigen *Clostridium tyrobutyricum*. The tubes were maintained at a temperature of 37° C. Twenty one hours after the inoculation of the tube with the bacteria, the different crotonate derivatives from Table 1 were added to different tubes in the amounts indicated in Table 6. This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 54 hours. Growth at the intervals was measured by reading the optical density (OD) of the fermentation liquid. Optical density was measured as described in Example 1. The ability of a tube fermentation at a particular concentration of crotonate derivative to reach a predetermined optical density was recorded in Table 6. Table 6 indicates the presence of bacterial growth to an OD of approximately 1.8 or above with a "+", and to an optical density in a range of 0.7 to 1.5 as a +/−, and indicates the failure of bacterial growth to reach an optical density of approximately 0.7 as a "−".

TABLE 6

| ppm | 0 | 100 | 500 | 1000 |
|---|---|---|---|---|
| A | + | + | +/− | − |
| B | + | + | + | + |
| C | + | + | + | + |
| D | + | + | + | + |
| E | + | + | + | + |
| F | + | + | + | + |
| G | + | + | + | + |

Example 4

Similar experiments were conducted to determine the effect of the crotonate derivatives on heteroacetogenic bacteria. Selected crotonate derivatives were tested in a series of batch experiments to determine the growth response of butyrigens to the presence of the compounds at varying concentrations. The batch experiments were all conducted by anoxically filling a 20 ml Balch tube with 5 ml of a fermentation medium having the composition given in Tables 2 and 3. The media included 0.5 v/v final concentration of a fructose substrate. For each of the crotonate concentrations tested, duplicate test tubes were prepared.

Each tube was inoculated with 0.5 ml of the heteroacetogenic bacteria *Clostridium Carboxydivorans*. The tubes were maintained at a temperature of 37° C. At a time 20 hours after the inoculation of the bacteria different crotonate derivatives from Table 1 were added to different tubes in the amounts indicated in Table 7. This was at a time of early to mid-log phase growth. Each fermentation of the bacteria in the media at the different concentration of crotonate derivatives were allowed to progress and were monitored to determine the bacteria growth at selected intervals of time varying from approximately 20 hours to 54 hours. Growth at the different intervals was measured by reading the optical density (OD) of the fermentation liquid. Optical density was measured as described in Example 1. The ability of a tube fermentation at a particular concentration of crotonate derivative to reach a predetermined optical density was recorded in Table 7. Table 7 indicates the presence of bacterial growth to an OD of approximately 1.8 with a "+". For these experiments the +/− indicates that one duplicate test tube showed a + indication and the other showed an optical density of less than 0.5.

TABLE 7

| ppm | 0 | 100 | 500 | 1000 |
|---|---|---|---|---|
| A | + | + | + | + |
| D | + | + | + | +/− |

Product profiles were determined on the *C. carboxidivorans* cultures that grew in the presence of compound A. A GC-MSD was performed on 54 hour cultures and product distributions were calculated based on the resultant areas of the output (See FIG. 2). In cultures with no compound A addition, the distribution of $C_2$, $C_4$ and $C_6$ acids and alcohols was similar in both samples. As the compound A concentration increased the amount of $C_2$, particularly the alcohols, increased. At 500 and 1000 ppm virtually all the product observed was the $C_2$ alcohol. Thus the presence of compound A shows the inhibitory effect on $C_4$ and longer chain alcohol and acid production. Thus, such crotonate derivatives can effectively limit the amount of butyl impurity accumulation in the fermentation zone from heteroacetogens which can compete effectively in syngas cultures with homoacetogenic bacteria.

Example 5

Compound A was tested again in set of experiments in all respects the same as that described for Example 4 except that compound A was added to Balch tubes in the amounts indicated in Table 7 at a time 5.5 hours after the inoculation of the bacteria. This was at a time in early log phase growth. In this case the Balch tube that contained no compound A reached an OD of 2 after 29 hours or less. After about 54 hours the tube fermentations that received 100 ppm of compound A had one tube reach an OD of at least 2 while the duplicate tube failed to reach an OD of 1. For all the fermentation tubes that received 500 and 1000 ppm of compound A, the OD failed to rise above about 0.5.

Examples 1-5 showed that compounds A and D were both tolerated by the homoacetogens at concentration of up to 1000 ppm. Both of compounds A and D showed inhibition effect for reducing butyrigen growth. Thus, the dihalogenated crotonyl esters and acids were shown to have useful in-vivo inhibition effects for reducing butyl impurities in homoacetogenic fermentations for the production of ethanol and acetic acid.

Examples 6-10

Additional experiments were conducted to determine the effect of the crotonyl derivatives in continuous fermentations containing butyrigen contamination. Compounds A and D were tested in a 2-L fermenter containing a seed culture from a 10,000 gallon bioreactor used in a large scale fermentation run. The large scale fermentation run had a fermentation liquid volume of approximately 8,000 gallons. The large scale fermentation run was grown from an inoculation of *Clostridium Autoethanogenum* that showed a significant presence of buytrigen by the presence of 0.5% butyl compounds in its products.

Figure 3:
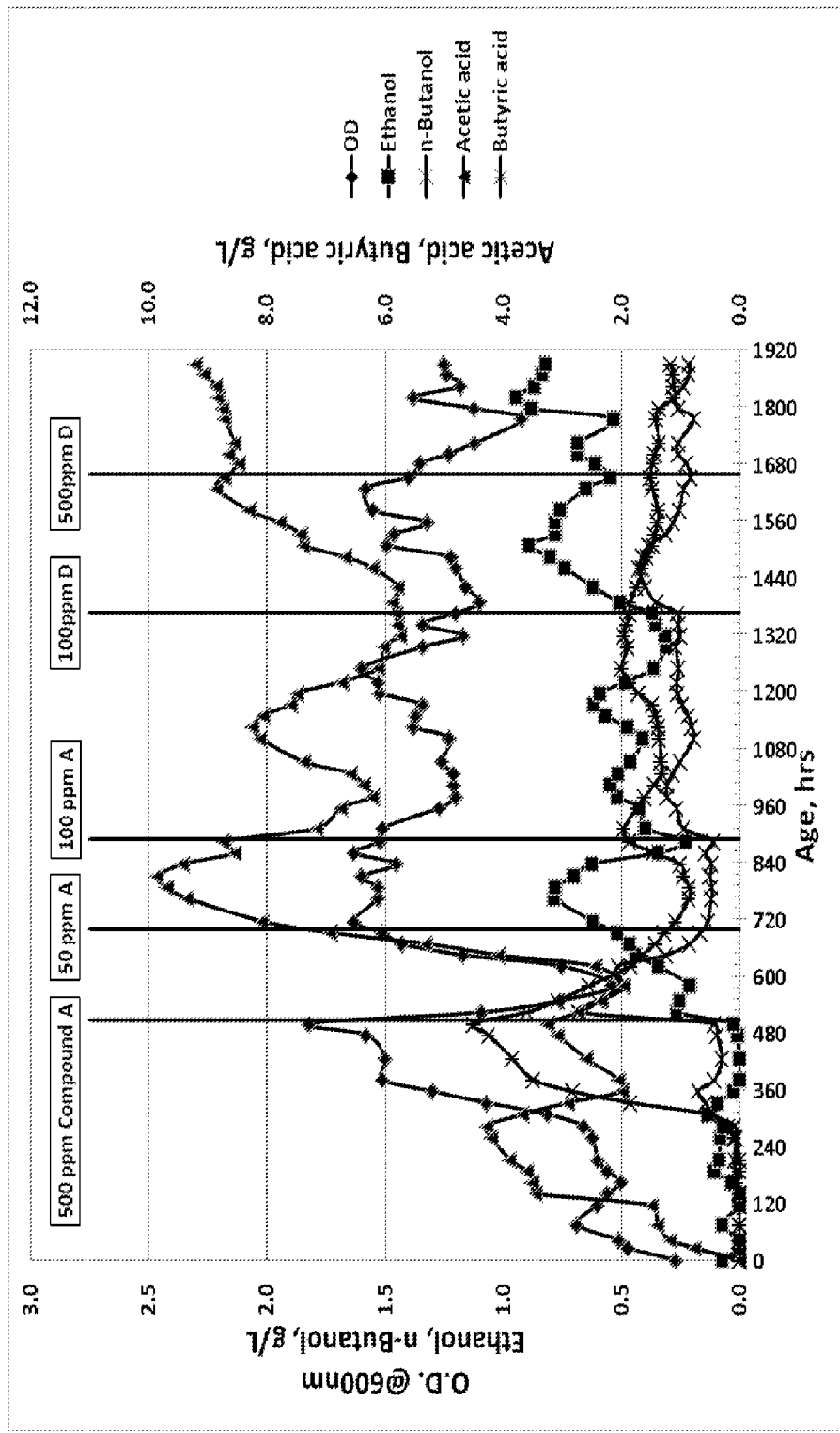
FIG. 3 is a plot showing the concentration of acetate and butyrate compounds over time in a continuous fermenter run along with the optical density of the fermentation liquid.

To initiate the 2 liter fermentation a seed culture from the large scale fermenter was introduced into the 2 liter fermenter and grown on yeast extract to an OD greater than 1 at which time a substantial production of butyrigens was observed. The 2 liter fermenter was a Sartorius Biostat B Series fermenter that operated as a continuously stirred tank with a mixing speed of 200 rpm. After 24 hours of initial growth a gas stream having a composition 38% CO, 38% $H_2$, 15% $CO_2$ and the balance $CH_4$ was introduced into the fermenter. The fermentation was conducted at a temperature of 37° C., a pH of 5.30±0.05 and contained approximately 2 liters of fermentation media having a composition found in Table 8. Fresh fermentation media was continually added to the 2 liter fermenter at rate sufficient to establish a mean cell retention time of 5.8 days. The fermentation was allowed to progress and different concentrations of the compounds A and D were added to the fermentation as intermittent injections at different times. Each injection was allowed to wash out of the fermenter before next injection. The presence of acetate and butyrate compounds in the fermenter along with the OD of the fermentation media are shown in FIG. 3.

TABLE 8

2-liter Fermentation Medium Composition

| Components | Amount per liter |
|---|---|
| Mineral solution, See Table 7(a) | 25 ml |
| Trace metal solution, See Table 7(b) | 10 ml |
| Vitamins solution, See Table 7(c) | 10 ml |
| Yeast Extract | 0 g |
| Adjust pH with NaOH | 6.1 |
| Reducing agent, See Table 2(d) | 2.5 ml |

TABLE 7(a)

Mineral Solution

| Components | Concentration (g/L) |
|---|---|
| NaCl | 0 |
| $NH_4Cl$ | 100 |
| KCl | 10 |
| $KH_2PO_4$ | 20 |
| $MgSO_4 \cdot 7H_2O$ | 5 |
| $CaCl_2 \cdot 2H_2O$ | 2 |

TABLE 7(b)

Trace Metals Solution

| Components | Concentration (g/L) |
|---|---|
| Nitrilotriacetic acid | 0 |
| pH 2.0 with 12.1 N HCL | |
| $MnSO_4 \cdot H_2O$ | 0.377 |
| $Fe(NH_4)_2(SO_4)_2 \cdot 6H_2O$ | 0 |
| $CoCl_2 \cdot 6H_2O$ | 0.358 |
| $ZnSO_4 \cdot 7H_2O$ | 1.96 |
| $NiCl_2 \cdot 6H_2O$ | 0.078 |
| $Na_2MoO_4 \cdot 2H_2O$ | 0 |
| $Na_2SeO_4$ | 0.1 |
| $Na_2WO_4$ | 0.118 |
| $Fe(SO4) \cdot 7H2O$ | 3.657 |
| pH 2.0 with 12.1 N HCL | |

TABLE 7(c)

Vitamin Solution

| Components | Concentration (mg/L) |
|---|---|
| Pyridoxine•HCl | 0 |
| Thiamine•HCl | 10 |
| Riboflavin | 0 |
| Calcium Pantothenate | 10 |
| Thioctic acid | 0 |
| p-Aminobenzoic acid | 0 |
| Nicotinic acid | 0.5 |
| Vitamin B12 | 0 |
| Mercaptoethanesulfonic acid | 0 |
| Biotin | 5 |
| Folic acid | 0 |

TABLE 7(d)

Reducing Agent

| Components | Concentration (g/L) |
|---|---|
| Cysteine (free base) | 40 |
| $Na_2S \cdot 9H_2O$ | 0 |
| Clerol antifoam | 0.02 |

Example 6

Figure 4:
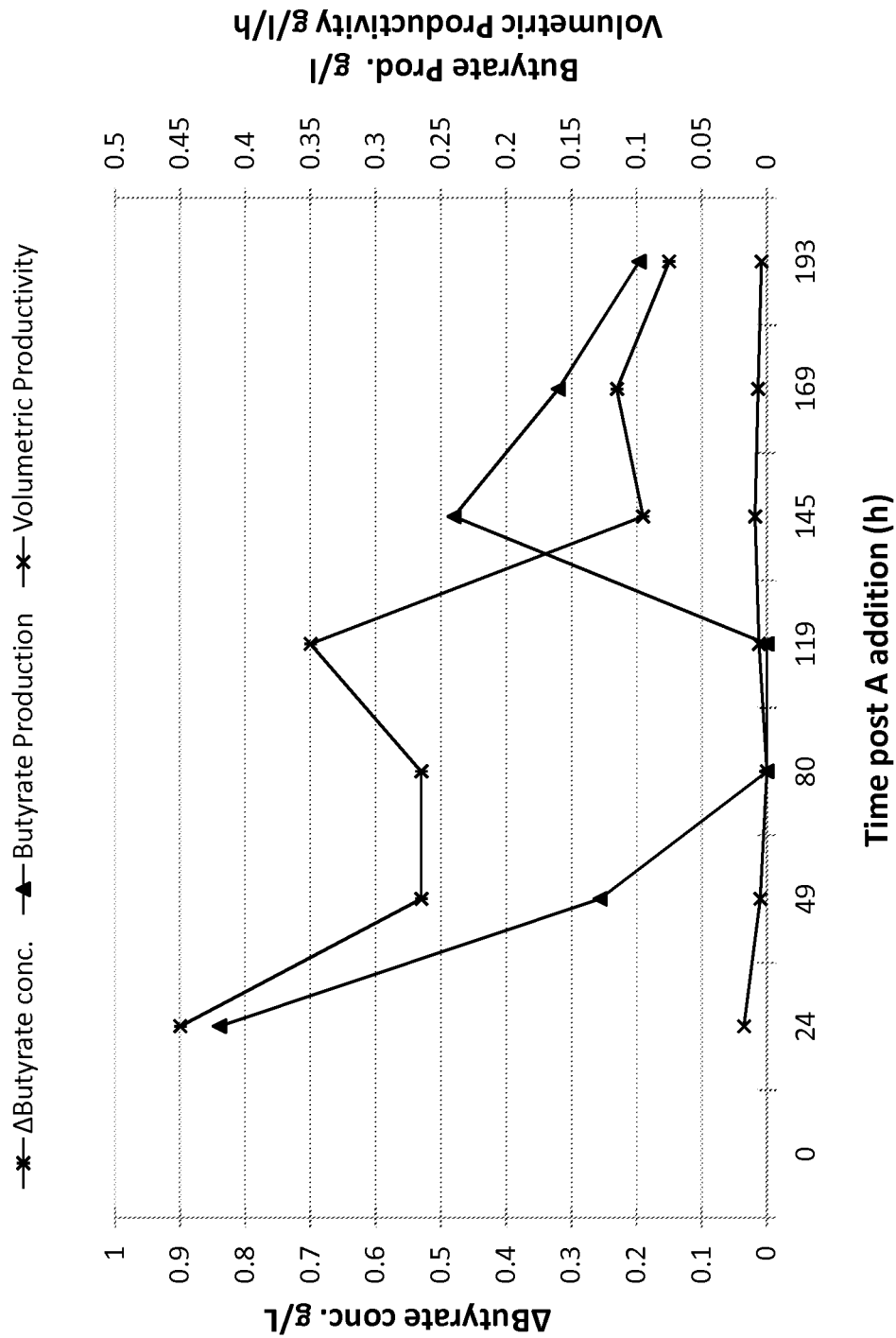
FIG. 4 is a plot showing the production and production rate of butyrate compounds over a selected time period from the continuous fermenter run of FIG. 3.
Figure 5:
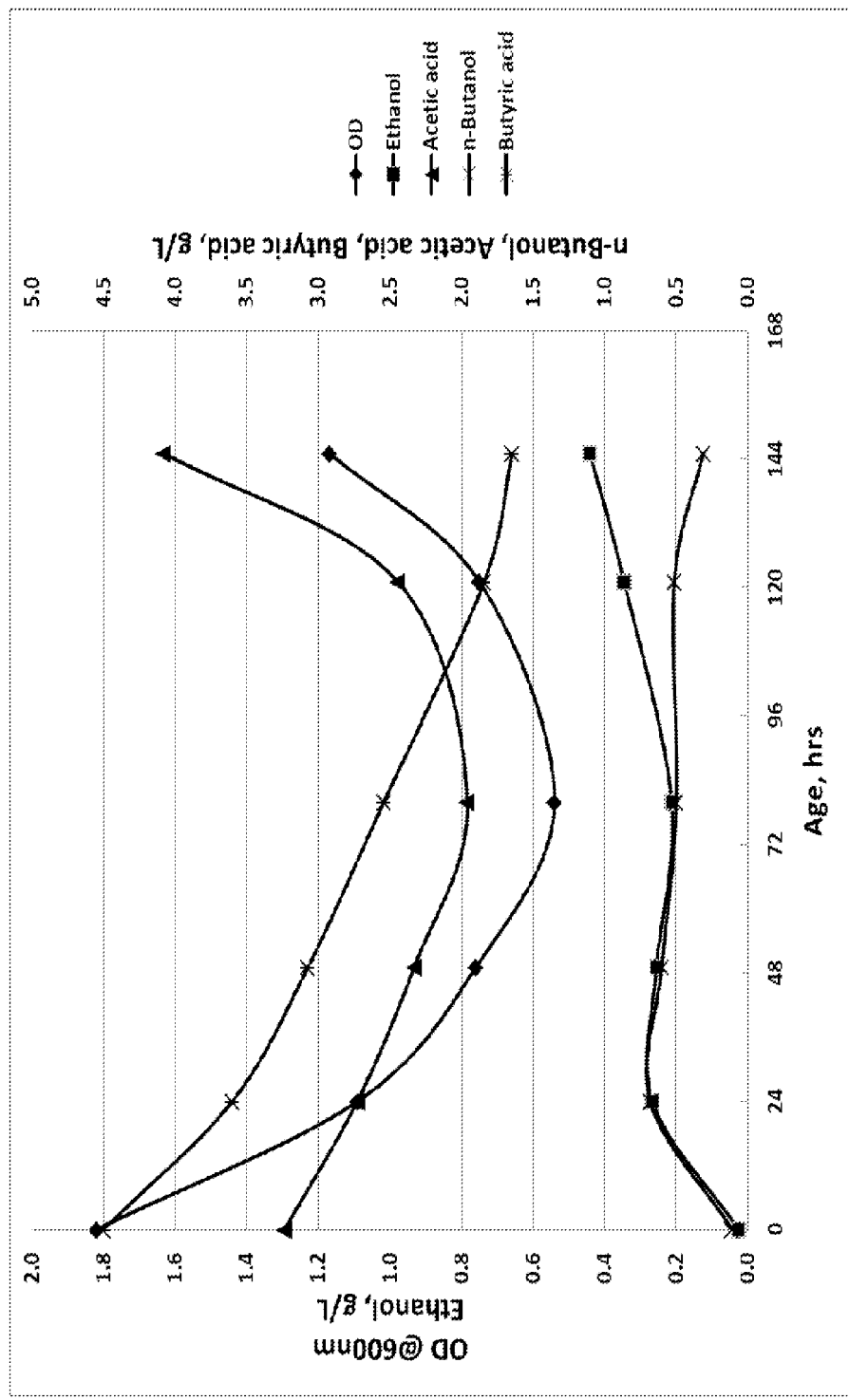
FIG. 5 is an expanded portion of the plot of FIG. 3 between approximately 500 hours and 640 hours.

After approximately 500 hours of fermenter operation compound A was added directly into the fermenter to a concentration of 500 ppm when the OD was 1.82 and butyrate concentration was 4.5 g/L. Following introduction of the compound, the OD decreased rapidly by almost 50% in the first 24 hours and the butyrate concentration decreased by 20% in the same time period. Also in the first 24 hours the butanol content increased rapidly by 6-fold to 0.68 g/L, indicating rapid conversion of the butyric acid to butanol. The rate of conversion of the butyric acid and the dilution rate of the media combined to dramatically decrease the butyrate production rate until it was brought down to zero within 80 hours of initially adding compound A. (See FIG. 4) In addition the OD continued to decrease to a low of 0.54 after 80 hours. Approximately 140 hours after the 500 ppm addition of compound A the OD nearly recovered to its original level with an increase in ethanol of over 100% and a dramatic rise in acetic acid production. (See FIG. 5) The concentration of the $C_2$ and $C_4$ alcohols and acids are shown in Table 9.

TABLE 9

| Addition Hr | OD @ 600 nm | Ethanol g/L | Acetic acid g/L | n-Butanol g/L | Butyric acid g/L |
|---|---|---|---|---|---|
| 0.0 | 1.82 | 0.026 | 3.237 | 0.109 | 4.503 |
| 24.0 | 1.09 | 0.266 | 2.728 | 0.681 | 3.600 |
| 49.0 | 0.76 | 0.255 | 2.333 | 0.601 | 3.074 |
| 80.0 | 0.54 | 0.212 | 1.959 | 0.497 | 2.542 |
| 121.0 | 0.75 | 0.345 | 2.446 | 0.513 | 1.842 |
| 145.0 | 1.17 | 0.441 | 4.082 | 0.311 | 1.645 |

Example 7

After approximately 700 hours of fermenter operation and the washout of the first 500 ppm addition of compound A, another 50 ppm of compound A was added directly into the fermenter. A decrease in OD and butyrate concentration (See FIG. 3) followed the 50 ppm addition and continued for at least for the first 3 days. At the same time there was a continued increase in the concentration of ethanol and acetic acid.

Example 8

After approximately another 8 days and the washout of the 50 ppm addition of compound A, the butyrate concentration increased to 2 g/L. At this time another 100 ppm of compound A was added directly into the fermenter approximately 890 hours into the run. Upon addition of compound A the ethanol concentration began to immediately increase. After about 24 hours, the butyrate concentration began to decrease again declining almost 50% over the next 4 days. (See FIG. 3)

The results of Examples 5-8 show that in a 2-L butyrogenic reactor compound A had an inhibitory and bactericidal effect on the butyrigen population shortly after addition. In all three trials, addition of compound A showed a decrease in the first 24 hours in both OD and butyrate production with an increase in C2 production. The addition of the butyrigen retardant was shown to have beneficial effects at concentrations as low as 50 ppm.

Example 9

Fermenter operation was continued under the same operating conditions following the 100 ppm addition of compound A. After allowing 20 days for the complete wash out of compound A, 100 ppm of compound D was added directly into the fermenter approximately 1370 hours into the fermenter run. Upon the addition of compound D there was a sharp rise in the ethanol concentration and acetic acid concentration accompanied by a decrease in the butyrate production. The butanol concentration rose temporarily following the 100 ppm addition of compound D which again is believed to show a rapid conversion of the butyric acid to butanol as was seen in Example 5.

Example 10

For 12 days after the first injection of compound D into the fermenter, the fermenter was allowed to wash out compound D. Then 500 ppm of compound D was injected directly into the fermenter after about 1660 hours of fermenter operation. (See FIG. 3) The resulting concentrations of the $C_2$ and $C_4$ alcohols and acids from the time of adding the 500 ppm of compound D are shown in Table 10.

TABLE 10

| Addition Hr | OD @ 600 nm | EtOH g/L | Acetic acid g/L | n-Butanol g/L | Butyric acid g/L |
|---|---|---|---|---|---|
| 0 | 1.40 | 0.55 | 8.72 | 0.21 | 1.51 |
| 30 | 1.35 | 0.61 | 8.48 | 0.23 | 1.47 |
| 49 | 1.23 | 0.69 | 8.64 | 0.26 | 1.44 |
| 73 | 1.12 | 0.68 | 8.56 | 0.26 | 1.37 |
| 123 | 0.92 | 0.53 | 8.72 | 0.19 | 1.41 |
| 145 | 1.12 | 0.88 | 8.75 | 0.26 | 1.36 |
| 168 | 1.38 | 0.95 | 8.83 | 0.28 | 1.11 |
| 193 | 1.18 | 0.87 | 8.86 | 0.24 | 1.12 |
| 217 | 1.24 | 0.84 | 9.05 | 0.21 | 1.13 |
| 240 | 1.25 | 0.82 | 9.21 | 0.21 | 1.17 |

Figure 6:
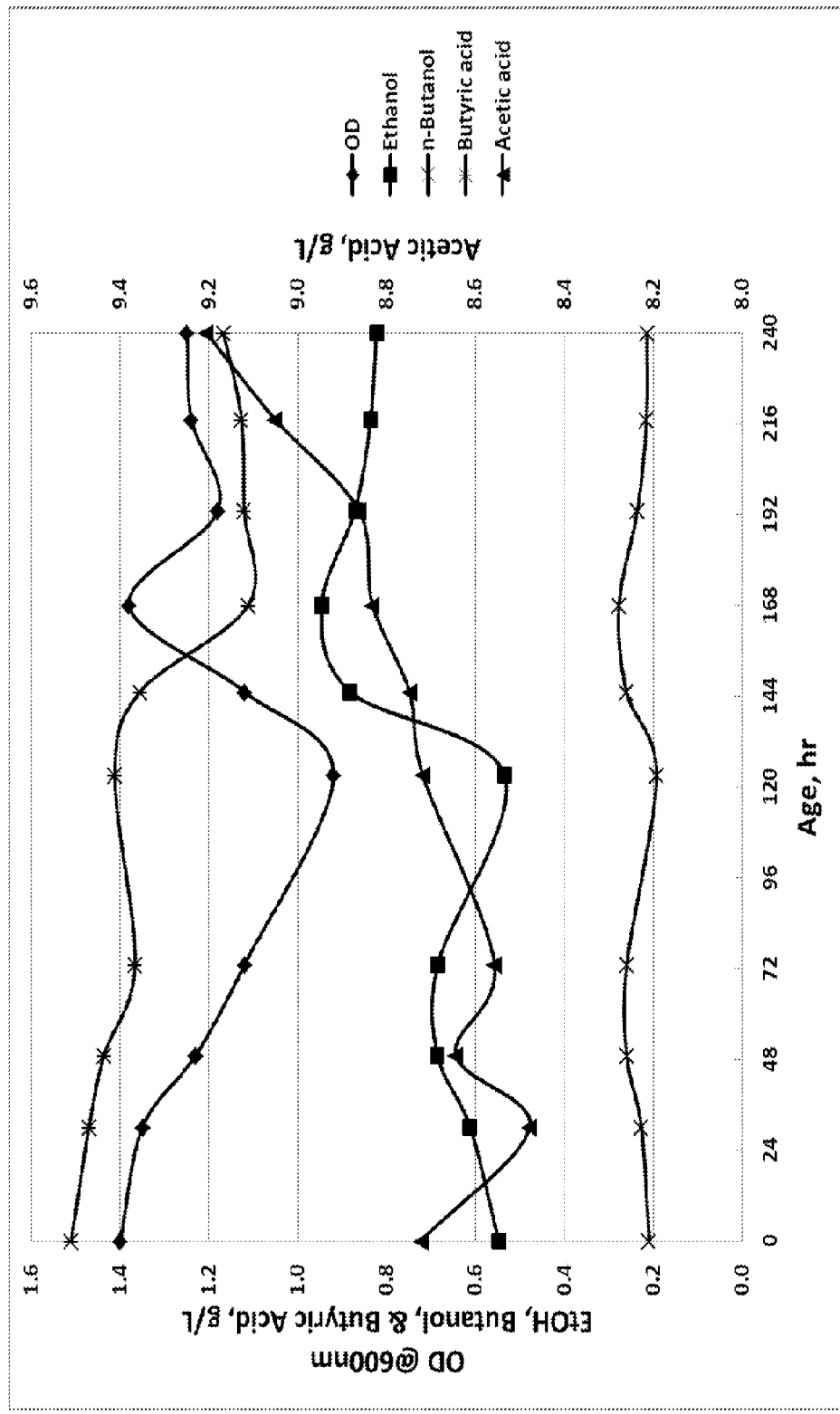
FIG. 6 is an expanded portion of the plot of FIG. 3 between approximately 1660 hours and 1900 hours.

The data and FIG. 6 show that immediately after addition of the compound D, the OD began to decrease showing reduction of cell growth. Furthermore, the concentrations of n-butyrate and n-butanol began to level off and slowly decrease whereas the concentrations of ethanol and acetate began to rise. Moreover, after the initial decrease, the OD began to rise with the concomitant increase of the $C_2$ compounds. This clearly established that the butyrigens were specifically inhibited whereas the homoacetogenic organisms were not inhibited and were able to grow and continue to produce the desirable $C_2$ products in the presence of compound D.

It is claimed:

1. A method of restricting the production of butyrate and butanol in an anaerobic fermentation of a gas substrate comprising at least one of CO and a mixture of $CO_2$ with hydrogen, the method comprising:
    passing the gas stream to an anaerobic fermentation zone containing at least one species of anaerobic microorganism capable of producing a liquid product comprising light oxygenates;
    converting at least a portion of the gas stream to the liquid product by contact of the microorganism in the fermentation zone with the gas stream;
    adding at least one of a 4,4,4, tri-halogen substituted 3(methyltri-halogen substituted) crotonate ester and a 4,4,4, tri-substituted halogen 3(methyltri-halogen substituted) crotonic acid to the fermentation liquid in an amount effective to restrict production of butyrate and butanol;
    withdrawing fermentation liquid containing the liquid product from the fermentation zone; and,
    recovering the liquid product from the fermentation liquid.

2. The method of claim 1 wherein the fermentation zone contains a homoacetogenic microorganism for the production of a liquid product comprising ethanol or acetate and is contaminated with a butyrigenic microorganism that produces at least one of butyrate or butanol.

3. The method of claim 1 wherein the fermentation zone contains a heteroacetogenic microorganism that produces at least one of acetic acid and ethanol as the liquid product and at least one of butyrate and butanol.

4. The method of claim 1 wherein the ethanol containing fermentation liquid contains less than 0.1% butyrate.

5. The method of claim 1 wherein the fermentation zone contains a homoacetogenic microorganism that comprises at least one of *Clostridium autoethanogenum*, *Clostridium ljungdahlii*, *Clostridium ragsdalei*, and *Clostridium coskatii* and the fermentation zone produces a liquid product comprising at least one of acetate and ethanol.

6. The method of claim 1 wherein the fermentation zone comprises a suspended cell bioreactor that suspends the anaerobic microorganism in the fermentation liquid and the at least one of the 4,4,4, tri-substituted halogen 3(methyltri-halogen substituted) crotonate ester and the 4,4,4, tri-substituted halogen 3(methyltri-halogen substituted) crotonic acid enters the bioreactor with a media mixture that flows into the fermentation liquid.

7. The method of claim 1 wherein the fermentation zone comprises a membrane supported bioreactor.

8. The method of claim 1 wherein the at least one of the 4,4,4, tri-substituted halogen 3(methyltri-halogen substituted) crotonate ester; and the 4,4,4, tri-substituted halogen 3(methyltri-halogen substituted) crotonic acid is at least one of Ethyl 4,4,4, Trifluoromethyl 3(trifluoromethyl)crotonate; 4,4,4,trifluoro 3-(trifluoromethyl)crotonic acid; and Ethyl 4,4,4,trifluoromethyl 3-(trichloromethyl) crotonate; 4,4,4, trifluoromethyl 3-(trichloromethyl)crotonic acid; Ethyl 4,4,4 trichloromethyl 3-(trifluoromethyl)crotonate; 4,4,4 trichloromethyl 3-(trifluoromethyl)crotonic acid; Ethyl 4,4,4 trichloromethyl 3-(trichloromethyl)crotonate; and 4,4,4 trichloromethyl 3-(trichloromethyl)crotonic acid.

9. The method of claim 1 wherein the anaerobic microorganism is a heteroacetogen that produces liquid products having at least 2 to 3 carbon atoms and the liquid product comprises at least one of acetic acid, ethanol, propanol, and propionic acid.

10. The method of claim 1 wherein the at least one of the 4,4,4, tri-substituted halogen 3(methyltri-halogen substituted) crotonate ester and the 4,4,4, tri-substituted halogen 3(methyltri-halogen substituted) crotonic acid is added in an amount sufficient to produce a concentration of at least 10 ppm in the fermentation liquid.

11. The method of claim 1 wherein the at least one of the 4,4,4, tri-substituted halogen 3(methyltri-halogen substituted) crotonate ester and the 4,4,4, tri-substituted halogen 3(methyltri-halogen substituted) crotonic acid is added to the fermentation zone as single dose in an amount of at least 50 ppm.

12. The method of claim 1 wherein the fermentation zone comprises a membrane supported bioreactor and the at least one of the 4,4,4, tri-substituted halogen 3(methyltri-halogen substituted) crotonate ester and the 4,4,4, tri-substituted halogen 3(methyltri-halogen substituted) crotonic acid is added to the fermentation liquid.

13. A method of restricting the production of butyrate and butanol in an anaerobic fermentation of a gas substrate comprising at least one of CO and a mixture of $CO_2$ with hydrogen, the method comprising:
passing the gas stream to a fermentation zone containing more than one species of anaerobic microorganisms and a fermentation liquid;
converting the gas stream to a liquid product comprising a light oxygenate by contact of at least one of the anaerobic microorganisms in the fermentation zone with the gas stream;
adding an amount of at least one of a 4,4,4, tri-substituted halogen 3(methyltri-halogen substituted) crotonate ester and a 4,4,4, tri-substituted halogen 3(methyltri-halogen substituted) crotonic acid to the fermentation liquid to inhibit any production of butyrate or butanol from at least one species of microorganism in the fermentation zone liquid effective to restrict production of butyrate and butanol;
withdrawing fermentation liquid containing the liquid product from the fermentation zone; and,
recovering the liquid product from the fermentation zone.

14. The method of claim 13 wherein the ethanol containing fermentation liquid contains less than 0.1% butyrate.

15. The method of claim 13 wherein the fermentation zone contains a homoacetogenic microorganism for the production of a liquid product comprising ethanol and a butyrigenic microorganism that produces at least one of butyrate or butanol.

16. The method of claim 13 wherein the at least one of the 4,4,4, tri-substituted halogen 3(methyltri-halogen substituted) crotonate ester and the 4,4,4, tri-substituted halogen 3(methyltri-halogen substituted) crotonic acid is at least one of Ethyl 4,4,4, Trifluoromethyl 3(trifluoromethyl)crotonate; 4,4,4,trifluoro 3-(trifluoromethyl) crotonic acid; and Ethyl 4,4,4,trifluoromethyl 3-(trichloromethyl)crotonate.

17. The method of claim 13 wherein the anaerobic microorganism is a heteroacetogen that produces liquid products having at least 2 to 3 carbon atoms and the liquid product comprises at least one of acetic acid, ethanol, propanol, and propionic acid.

18. The method of claim 13 wherein the at least one of the 4,4,4, tri-substituted halogen 3(methyltri-halogen substituted) crotonate ester and the 4,4,4, tri-substituted halogen 3(methyltri-halogen substituted) crotonic acid is added to the fermentation liquid at a concentration of at least 10 ppm.

19. A method of producing a product comprising a $C_2$ oxygenate by the fermentation of a gas substrate comprising at least one of CO and a mixture of $CO_2$ with hydrogen using a homoacetogenic microorganism to convert the gas stream to the product, the method comprising:
passing the gas stream to a fermentation zone containing an anaerobic microorganism and a fermentation liquid;
converting the gas stream to the product by contact of the anaerobic microorganism in the fermentation zone with the gas stream;
adding an amount of at least one of a 4,4,4, tri-substituted halogen 3(methyltri-halogen substituted) crotonate ester and a 4,4,4, tri-substituted halogen 3(methyltri-halogen substituted) crotonic acid to the fermentation liquid sufficient to restrict production of butyrate and butanol;
withdrawing a product containing fermentation liquid from the fermentation zone; and,
recovering the product from the fermentation liquid.

20. The method of claim 19 wherein the at least one of the 4,4,4, tri-substituted halogen 3(methyltri-halogen substituted) crotonate ester and the 4,4,4, tri-substituted halogen 3(methyltri-halogen substituted) crotonic acid is added in at least one dose in an amount sufficient to produce a concentration of at least 10 ppm in the fermentation zone.

21. The method of claim 4-19 wherein the at least one of the 4,4,4, tri-substituted halogen 3(methyltri-halogen substituted) crotonate ester and the 4,4,4, tri-substituted halogen 3(methyltri-halogen substituted) crotonic acid is at least one of Ethyl 4,4,4, Trifluoromethyl 3(trifluoromethyl)crotonate; 4, 4, 4,trifluoro 3-(trifluoromethyl)crotonic acid; Ethyl 4,4,4, trifluoromethyl 3-(trichloromethyl)crotonate; 4,4,4, trifluoromethyl 3-(trichloromethyl)crotonic acid; Ethyl 4,4,4 trichloromethyl 3-(trifluoromethyl)crotonate; 4,4,4 trichloromethyl 3-(trifluoromethyl)crotonic acid; Ethyl 4,4,4 trichloromethyl 3-(trichloromethyl)crotonate; and 4,4,4 trichloromethyl 3-(trichloromethyl)crotonic acid.

* * * * *